US010722362B2

(12) United States Patent
Marr et al.

(10) Patent No.: US 10,722,362 B2
(45) Date of Patent: Jul. 28, 2020

(54) ADJUSTABLE AND REVERSIBLE LOCKING MECHANISM FOR CATHETER-DELIVERED IMPLANT

(71) Applicant: Edwards Lifesciences Corporation, Irvine, CA (US)

(72) Inventors: Devin H. Marr, Irvine, CA (US); David M. Taylor, Lake Forest, CA (US); Yoon H. Kwon, Mission Viejo, CA (US); Alexander J. Siegel, Costa Mesa, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 257 days.

(21) Appl. No.: 15/983,599

(22) Filed: May 18, 2018

(65) Prior Publication Data

US 2018/0333261 A1    Nov. 22, 2018

Related U.S. Application Data

(60) Provisional application No. 62/509,259, filed on May 22, 2017.

(51) Int. Cl.
*A61F 2/24* (2006.01)
*A61B 17/04* (2006.01)
*A61B 17/06* (2006.01)

(52) U.S. Cl.
CPC ........ *A61F 2/2463* (2013.01); *A61B 17/0469* (2013.01); *A61B 17/06166* (2013.01); *A61F 2/246* (2013.01); *A61F 2/2466* (2013.01); *A61F 2220/0008* (2013.01); *A61F 2230/0013* (2013.01)

(58) Field of Classification Search
CPC ...... A61F 2/2463; A61F 2/246; A61F 2/2466; A61F 2230/0013; A61F 2220/0008; A61B 17/0469; A61B 17/06166
See application file for complete search history.

(56) References Cited

U.S. PATENT DOCUMENTS

| 7,628,797 | B2 * | 12/2009 | Tieu ................... A61B 17/0487 24/129 R |
| 8,758,431 | B2 * | 6/2014 | Orlov ................. A61B 17/0057 623/2.11 |
| 9,913,717 | B2 * | 3/2018 | Chau ....................... A61F 2/246 |

(Continued)

FOREIGN PATENT DOCUMENTS

WO    2014189974 A1    11/2014

*Primary Examiner* — Julian W Woo (57) ABSTRACT

An implantable heart valve device has a main body including a first end portion and a second end portion. The main body is configured to be implanted around a native leaflet of a heart valve such that the first end portion is on an atrial side of the leaflet and the second end portion is on a ventricular side of the leaflet, and such that the main body can coapt with an opposing native leaflet during operation of the heart valve. One of the first or second end portions comprises a coupling assembly, and the other of the first or second end portions comprises a coupling member configured to extend through the native leaflet when the heart valve device is implanted in a heart valve. The coupling assembly is configured to releasably engage the coupling member to permit adjustment of the relative positions of the first and second end portions.

15 Claims, 6 Drawing Sheets

(56) References Cited

U.S. PATENT DOCUMENTS

| | | |
|---|---|---|
| 2002/0193871 A1 | 12/2002 | Beyersdorf et al. |
| 2005/0159810 A1 | 7/2005 | Filsoufi |
| 2008/0039935 A1 | 2/2008 | Buch et al. |
| 2009/0043381 A1 | 2/2009 | Macoviak et al. |
| 2015/0230919 A1 | 8/2015 | Chau et al. |

* cited by examiner

ADJUSTABLE AND REVERSIBLE LOCKING MECHANISM FOR CATHETER-DELIVERED IMPLANT

CROSS REFERENCE TO RELATED APPLICATION

This application claims the benefit of U.S. Provisional Application No. 62/509,259 filed on May 22, 2017, which is incorporated by reference herein in its entirety.

FIELD

This disclosure pertains to prosthetic devices and related methods for helping to seal native heart valves and reduce or prevent regurgitation therethrough, as well as devices and related methods for implanting such prosthetic devices.

BACKGROUND

The native heart valves (i.e., the aortic, pulmonary, tricuspid, and mitral valves) serve critical functions in assuring the forward flow of an adequate supply of blood through the cardiovascular system. These heart valves can be rendered less effective by congenital malformations, inflammatory processes, infectious conditions, or disease. Such damage to the valves can result in serious cardiovascular compromise or death. For many years the definitive treatment for such disorders was the surgical repair or replacement of the valve during open-heart surgery. However, such surgeries are highly invasive and are prone to many complications. Therefore, elderly and frail patients with defective heart valves often went untreated. More recently, transvascular techniques have been developed for introducing and implanting prosthetic devices in a manner that is much less invasive than open-heart surgery. Such transvascular techniques have increased in popularity due to their high success rates.

A healthy heart has a generally conical shape that tapers to a lower apex. The heart is four-chambered and comprises the left atrium, right atrium, left ventricle, and right ventricle. The left and right sides of the heart are separated by a wall generally referred to as the septum. The native mitral valve of the human heart connects the left atrium to the left ventricle. The mitral valve has a very different anatomy than other native heart valves. The mitral valve includes an annulus portion, which is an annular portion of the native valve tissue surrounding the mitral valve orifice, and a pair of cusps, or leaflets extending downward from the annulus into the left ventricle. The mitral valve annulus can form a D-shaped, oval, or otherwise out-of-round cross-sectional shape having major and minor axes. The anterior leaflet can be larger than the posterior leaflet, forming a generally C-shaped boundary between the abutting free edges of the leaflets when they are closed together.

When operating properly, the anterior leaflet and the posterior leaflet function together as a one-way valve to allow blood to flow only from the left atrium to the left ventricle. The left atrium receives oxygenated blood from the pulmonary veins. When the muscles of the left atrium contract and the left ventricle dilates, the oxygenated blood that is collected in the left atrium flows into the left ventricle. When the muscles of the left atrium relax and the muscles of the left ventricle contract, the increased blood pressure in the left ventricle urges the two leaflets of the mitral valve together, thereby closing the one-way mitral valve so that blood cannot flow back into the left atrium and is, instead, expelled out of the left ventricle through the aortic valve. To prevent the two leaflets from prolapse under pressure and folding back through the mitral valve annulus towards the left atrium, a plurality of fibrous cords called chordae tendineae tether the leaflets to papillary muscles in the left ventricle.

Mitral regurgitation occurs when the native mitral valve fails to close properly and blood flows into the left atrium from the left ventricle during the systole phase of the cardiac cycle. Mitral regurgitation is the most common form of valvular heart disease. Mitral regurgitation has different causes, such as leaflet prolapse, dysfunctional papillary muscles, and/or stretching of the mitral valve annulus resulting from dilation of the left ventricle. Mitral regurgitation at a central portion of the leaflets can be referred to as central jet mitral regurgitation, and mitral regurgitation nearer to one commissure (i.e., location where the leaflets meet) of the leaflets can be referred to as eccentric jet mitral regurgitation.

Some prior techniques for treating mitral regurgitation include stitching portions of the native mitral valve leaflets directly to one another. Other prior techniques include the use of a body implanted between the native mitral valve leaflets. Despite these prior techniques, there is a continuing need for improved devices and methods for treating mitral valve regurgitation.

SUMMARY

Certain embodiments of the disclosure concern devices and methods of adjustably and/or releasably fastening a prosthetic implant to a leaflet of a native heart valve. In a representative example, an implantable heart valve device comprises a main body including a first end portion and a second end portion. The main body is configured to be implanted around a native leaflet of a heart valve such that the first end portion is on an atrial side of the leaflet and the second end portion is on a ventricular side of the leaflet and such that the main body can coapt with and move away from an opposing native leaflet during operation of the heart valve. One of the first or second end portions comprises a coupling assembly, and the other of the first or second end portions comprises a coupling member configured to extend through the native leaflet when the heart valve device is implanted in a heart valve. The coupling assembly is configured to releasably engage the coupling member to permit adjustment of the relative positions of the first and second end portions.

In some embodiments, the coupling assembly comprises a pawl member pivotable between a first position and a second position, the pawl member being configured to engage the coupling member when the pawl member is in the first position.

In some embodiments, the coupling assembly further comprises a spring member configured to bias the pawl member toward the first position.

In some embodiments, the coupling member comprises a coil having a plurality of turns.

In some embodiments, the pawl member and the spring member are situated in a first cap member coupled to the first end portion of the implantable heart valve device, and the coupling member is coupled to a second cap member coupled to the second end portion of the implantable heart valve device.

In some embodiments, the pawl member is pivotable about a pivot member disposed in the first cap member.

In some embodiments, the first cap member is in fluid communication with the main body such that a guide wire can extend from the first cap member into the main body.

In some embodiments, the coupling member defines a lumen such that the guide wire can extend through the lumen of the coupling member.

In another representative embodiment, an assembly comprises an implantable heart valve device including a main body having a first end portion and a second end portion. The main body is configured to be implanted around a native leaflet of a heart valve such that the first end portion is on an atrial side of the leaflet and the second end portion is on a ventricular side of the leaflet and such that the main body can coapt with and move away from an opposing native leaflet during operation of the heart valve. The first end portion comprises a coupling assembly, and the second end portion comprising a coupling member configured to extend through the native leaflet when the heart valve device is implanted in a heart valve. The coupling assembly is configured to releasably engage the coupling member to permit adjustment of the relative positions of the first and second end portions. The assembly further comprises a catheter including a shaft having a distal end portion releasably couplable to the first end portion of the heart valve device.

In some embodiments, the catheter comprises a first actuator member movable between a proximal position and a distal position to selectively engage the coupling assembly such that the coupling assembly disengages from the coupling member when the first actuator member is in the distal position.

In some embodiments, the coupling assembly comprises a pawl member movable between a first position and a second position, the pawl member being configured to engage the coupling member when the pawl member is in the first position, and the first actuator member is configured to move the pawl member to the second position when the first actuator member engages the pawl member.

In some embodiments, the catheter further comprises a second actuator member movable between a proximal position and a distal position to selectively engage the coupling member.

In some embodiments, the assembly is configured such that distal motion of the second actuator member causes corresponding distal motion of the coupling member relative to the coupling assembly when the second actuator contacts the coupling member and the pawl member is in the second position.

In some embodiments, the distal end portion of the catheter member is releasably coupled to the first end portion of the heart valve device by suture.

In some embodiments, the first end portion of the heart valve device comprises a cap member, the distal end portion of the catheter comprises first and second arm portions, and the suture extends from a lumen defined in the first arm portion, through the cap member, and through a lumen defined in the second arm portion.

In some embodiments, the assembly further comprises a guide wire extending from the catheter, through the main body of the heart valve device, through the coupling member, and back into the catheter.

In another representative embodiment, a method comprises delivering an implantable heart valve device to a native heart valve of a patient's body via a guide wire formed in a loop and extending through a leaflet of the native heart valve such that first and second ends of the guide wire are located outside the patient's body. The method further comprises positioning a first end portion of the heart valve device on an atrial side of the leaflet. The first end portion includes a coupling assembly. The method further comprises positioning a second end portion of the heart valve device on a ventricular side of the leaflet such that a main body of the heart valve device can coapt with and move away from an opposing native leaflet during operation of the heart valve. The second end portion includes a coupling member. The method further comprises coupling the first end portion of the heart valve device to the second end portion of the heart valve device by inserting the coupling member through the leaflet such that the coupling assembly engages the coupling member.

In some embodiments, the coupling assembly comprises a pawl member, the coupling member comprises a coil member, and coupling the first and second end portions of the prosthetic device further comprises moving the coil member past the pawl member.

In some embodiments, the method further comprises uncoupling the pawl member from the coil member with a first actuator member of a delivery catheter coupled to the heart valve device.

In some embodiments, the method further comprises moving the coupling member in a direction toward the second end portion using a second actuator member of the delivery catheter.

The foregoing and other objects, features, and advantages of the disclosed technology will become more apparent from the following detailed description, which proceeds with reference to the accompanying figures.

DETAILED DESCRIPTION

Described herein are embodiments of prosthetic devices that are primarily intended to be implanted at one of the mitral, aortic, tricuspid, or pulmonary valve regions of a human heart, as well as apparatuses and methods for implanting the same. In certain embodiments, the prosthetic devices can be used to help restore and/or replace the functionality of a defective native mitral valve. The disclosed embodiments should not be construed as limiting in any way. Instead, the present disclosure is directed toward all novel and nonobvious features and aspects of the various disclosed embodiments, alone and in various combinations and sub-combinations with one another.

Figure 1:
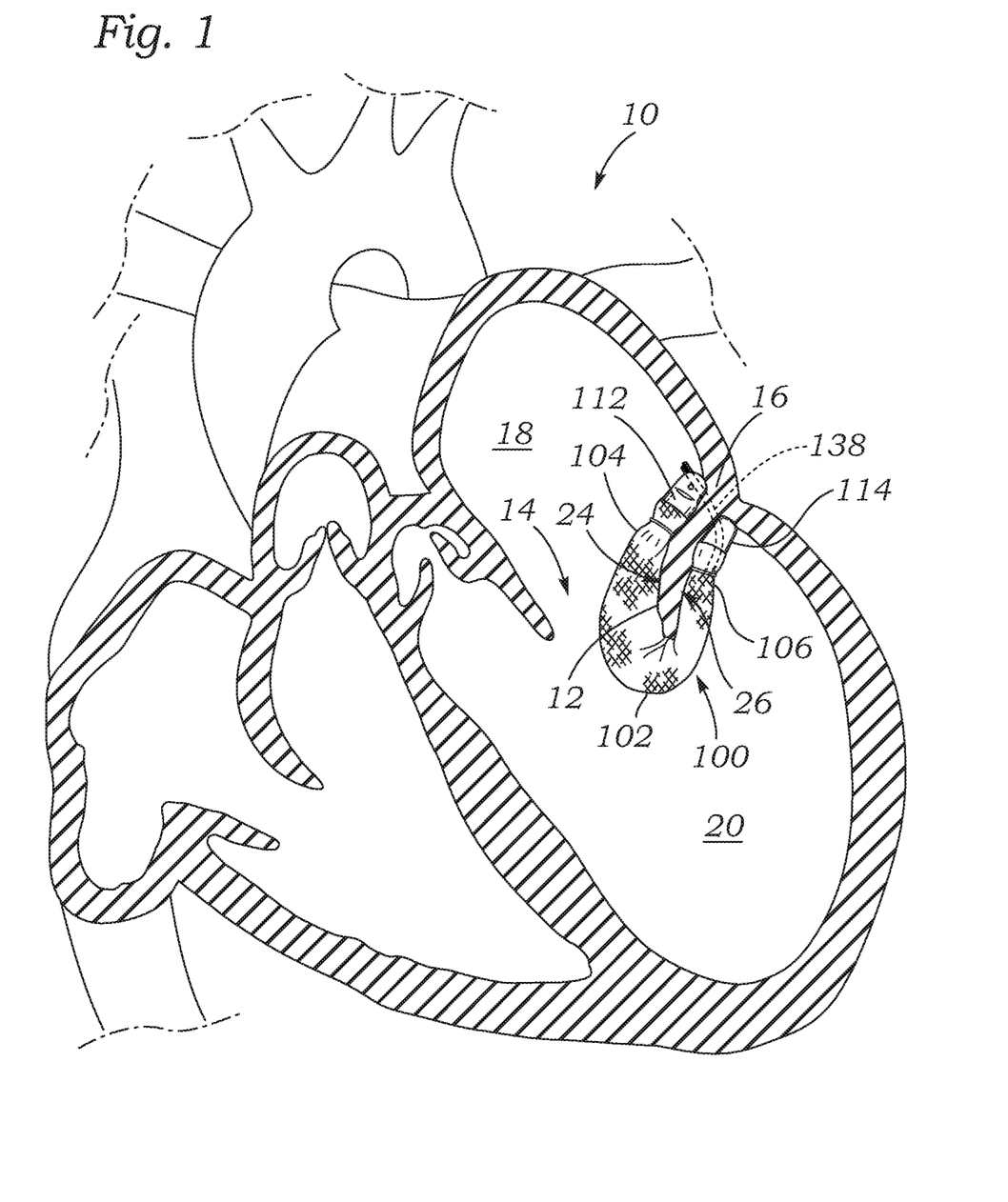
FIG. 1 is a cross-sectional view of a heart with a prosthetic device for treating mitral valve regurgitation implanted on the posterior mitral valve leaflet, according to one embodiment.

FIG. 1 illustrates a cross-sectional view of the human heart 10 with a prosthetic device 100 secured to a posterior leaflet 12 of the mitral valve 14, according to one embodiment. The prosthetic device 100 is configured to be implanted on a native leaflet of a heart valve so that it can coapt with an opposing leaflet of the heart valve to improve coaptation and reduce regurgitation. For example, when implanted on the posterior leaflet 12 as shown, the prosthetic device 100 can coapt with the native anterior leaflet. In other embodiments, the prosthetic device 100 can be implanted on the anterior leaflet and can coapt with the posterior leaflet.

The device can comprise a main body 102 including a first end portion 104 and a second end portion 106. In the deployed configuration, the main body 102 may be wrapped or otherwise disposed around the leaflet 12 such that the first end portion 104 is disposed in the left atrium 18 on the atrial side of the leaflet and covers an atrial surface 24 of the leaflet 12, and the second end portion 106 is disposed in the left ventricle 20 on the ventricular side of the leaflet and covers a ventricular surface 26 of the leaflet.

Figure 2:
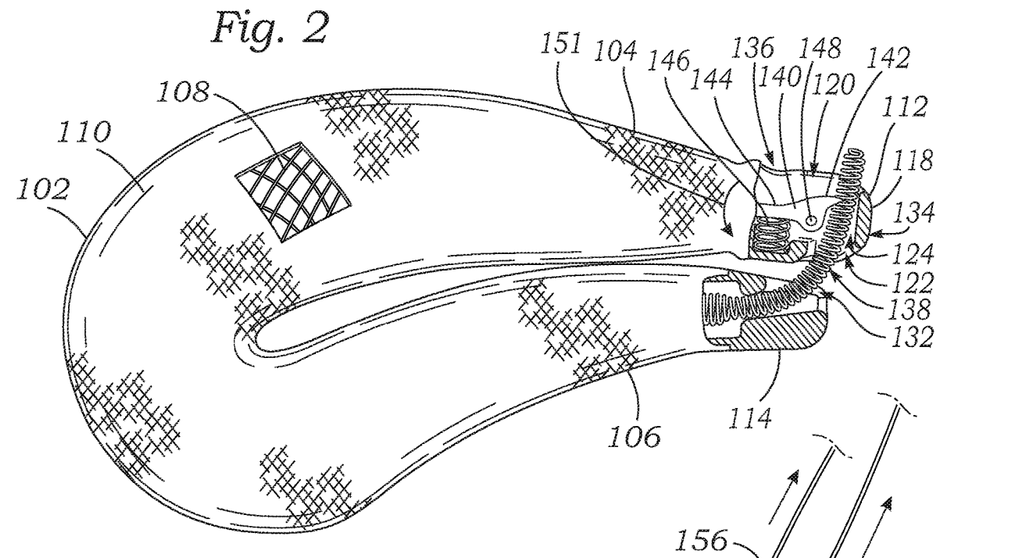
FIG. 2 is a perspective view of the prosthetic device of FIG. 1 including a coupling mechanism for coupling the first and second end portions of the device to each other.
Figure 3:
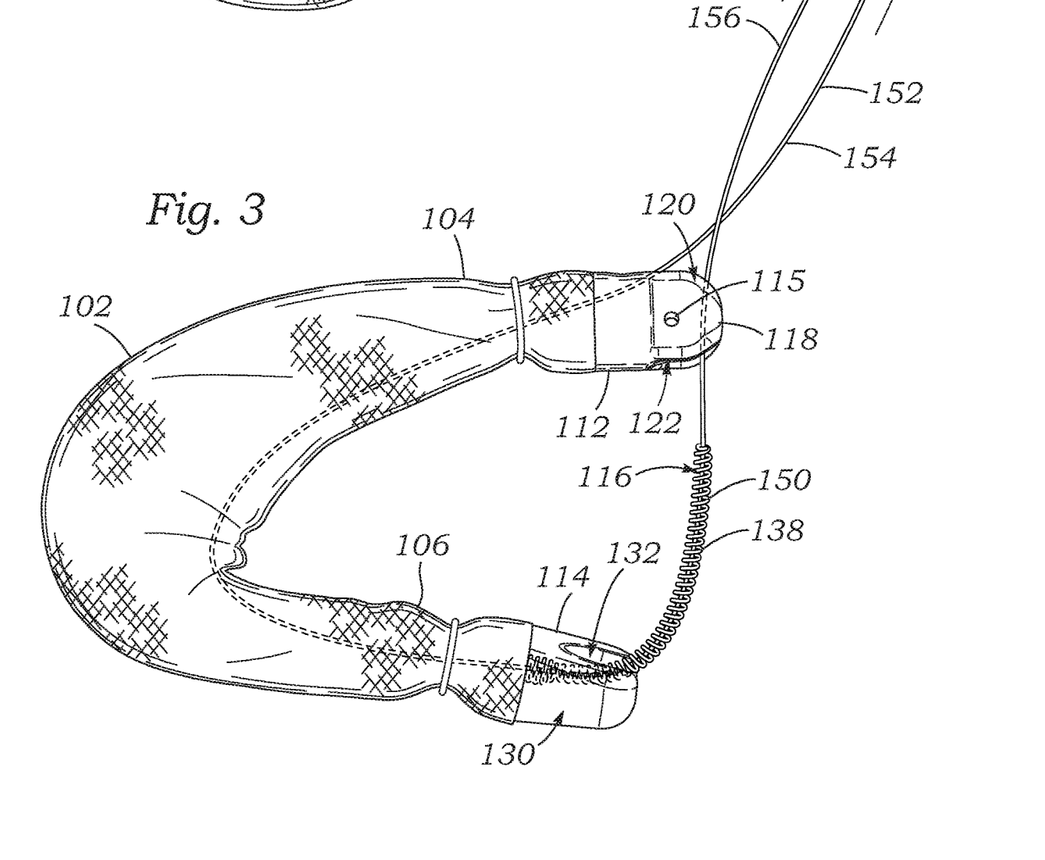
FIG. 3 is a perspective view of the prosthetic device of FIG. 1 illustrating a guide wire passing through the device with the first and second end portions in an uncoupled state.

FIGS. 2 and 3 illustrate the device 100 in greater detail. In the illustrated embodiment, main body 102 can comprise a tubular braided mesh 108 covered by an atraumatic covering 110. The braided mesh 108 can be made of Nitinol or other resiliently deformable and/or shape-settable material that can regain a desired shape when released from a delivery catheter or sheath inside the heart. In some embodiments, the braided mesh 108 and the covering 110 can allow the main body 102 to expand laterally when it is shortened longitudinally, and to contract laterally when it is lengthened longitudinally, as further described in U.S. Patent Application Publication No. 2015/0230919, which is incorporated herein by reference. In some embodiments, the braided mesh 108 can be shape-set to have a curved shape when in a non-deflected state.

Referring to FIGS. 2 and 3, the first end portion 104 can include a cap member 112, and the second end portion 106 can include a cap member 114. As illustrated in FIG. 2, the cap member 112 can be coupled to the main body of the implant 100 (e.g., to the braided mesh 108), and can include a housing portion 118. The housing portion 118 can define a first opening 120, a second opening 122, and a passage 124 extending between the openings 120, 122. In some embodiments, the cap member 112 can be open to the interior of the main body 102 such that the housing portion 118 and the main body of the implant are in fluid communication with each other. The cap member 112 can also define openings, such as opening 115 (FIG. 3), extending laterally through the housing portion 118, and through which suture can be threaded to couple the implant 100 to a delivery catheter, as further described below. As best shown in FIG. 3, the cap member 114 can define an internal passage 130, and a slot 132 extending along an upper surface of the cap member 114.

Referring again to FIG. 2, the device 100 can comprise a coupling mechanism generally indicated at 134 configured to releasably and/or adjustably couple the first and second end portions 104, 106 together, and to permit adjustment of the relative positions of the end portions 104, 106 at the treatment site. For example, in the illustrated configuration the coupling mechanism 134 can comprise a coupling assembly 136 configured to engage a coupling member 138. In some embodiments, the coupling assembly 136 can be incorporated into the first end portion 104 of the device, while the coupling member 138 can be coupled to the second end portion 106, and can extend from the second end portion to engage the coupling assembly.

For example, in the illustrated configuration, the coupling assembly 136 is situated in the internal passage 124 of the cap member 112. The coupling assembly 136 can comprise a pawl member 140 movable between a first position (FIG. 7) and a second position (FIG. 8). The pawl member 140 can comprise a first end portion 142 configured to engage the coupling member 138, and a second end portion 144 configured to engage a spring member 146. The pawl member 140 can be configured to pivot about a pivot member 148. The spring member 146 can be configured to bias the pawl member 140 toward the first position. Application of force to the second portion 144 of the pawl member 140 can compress the spring member 146, and cause the pawl member to pivot toward the second position.

In the illustrated embodiment, the coupling member 138 is configured as a coil including a plurality of turns 150 (FIG. 3). The coupling member 138 can be coupled to the cap member 114, and can extend through the slot 132 when engaged with the coupling assembly 136. In some embodiments, the coupling member 138 can be flexible such that it can move relative to the cap member 114 within the slot 132. In certain configurations, an end portion 116 (FIG. 3) of the coupling member 138 opposite the cap member 114 can also be tapered to facilitate insertion of the coupling member through the tissue of a native leaflet. For example, in certain configurations, one or more turns 150 of the coil can be ground such that the end portion 116 of the coil has a tapered profile. In certain embodiments, the coupling member 138 and/or the pawl member 140 can be made from any of various biocompatible metals or metal alloys, such as nickel-titanium alloys (e.g., Nitinol), stainless steel, cobalt-chromium alloys, etc.

Referring again to FIGS. 2 and 3, the pawl member 140 can be configured to engage the turns 150 of the coupling member 138. Motion of the coupling member 138 in the direction of arrow 151 (FIG. 2) can cause the pawl member 140 to pivot counterclockwise, compressing the spring member 146, and allowing successive turns 150 of the coupling member to advance past the pawl member. In this manner, the portion of the length of the coupling member 138 that advances past the pawl member 140 can be adjusted.

Figure 4:
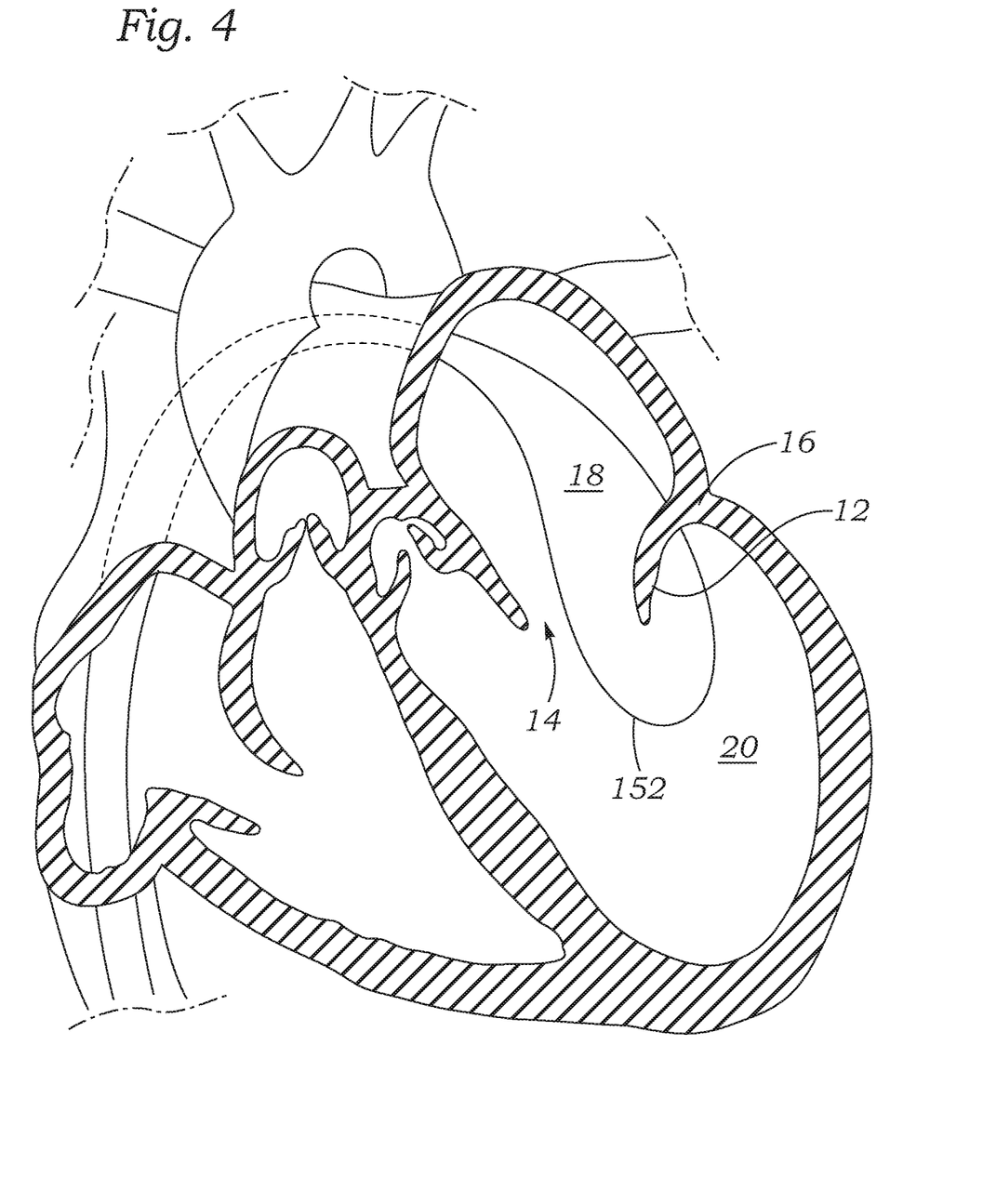
FIG. 4 is a cross-sectional view of a heart illustrating a guide wire extending through a native leaflet of the mitral valve to form a loop.

The implant 100 can be delivered using a guide wire or suture that is advanced transseptally to the left ventricle, inserted through the target leaflet (e.g., near the base of the leaflet adjacent the annulus of the native valve), and looped back through the patient's body to the access site, as described in detail in U.S. Patent Application Publication No. 2015/0230919 incorporated by reference above. In this manner, the guide wire forms a loop with both ends of the wire located outside the patient's body. FIG. 4 illustrates such a guide wire 152 extending through the native leaflet 12 adjacent the valve annulus 16 to form a loop.

The guide wire 152 can extend through the implant 100 such that the implant can be advanced to the treatment site along the guide wire. For example, with reference to FIG. 3, a first portion 154 of the guide wire 152 can extend through the opening 120 into the passage 124 (FIG. 2) of the cap member 112, and through the main body 102 of the implant. The guide wire 152 can extend through the cap member 114, and coaxially through the coupling member 138. The guide wire 152 can then extend back through the cap member 112 from the opening 122 to the opening 120, such that a second portion 156 of the guide wire emerges from the cap member 112 and extends back through the patient to the access site.

Figure 5:
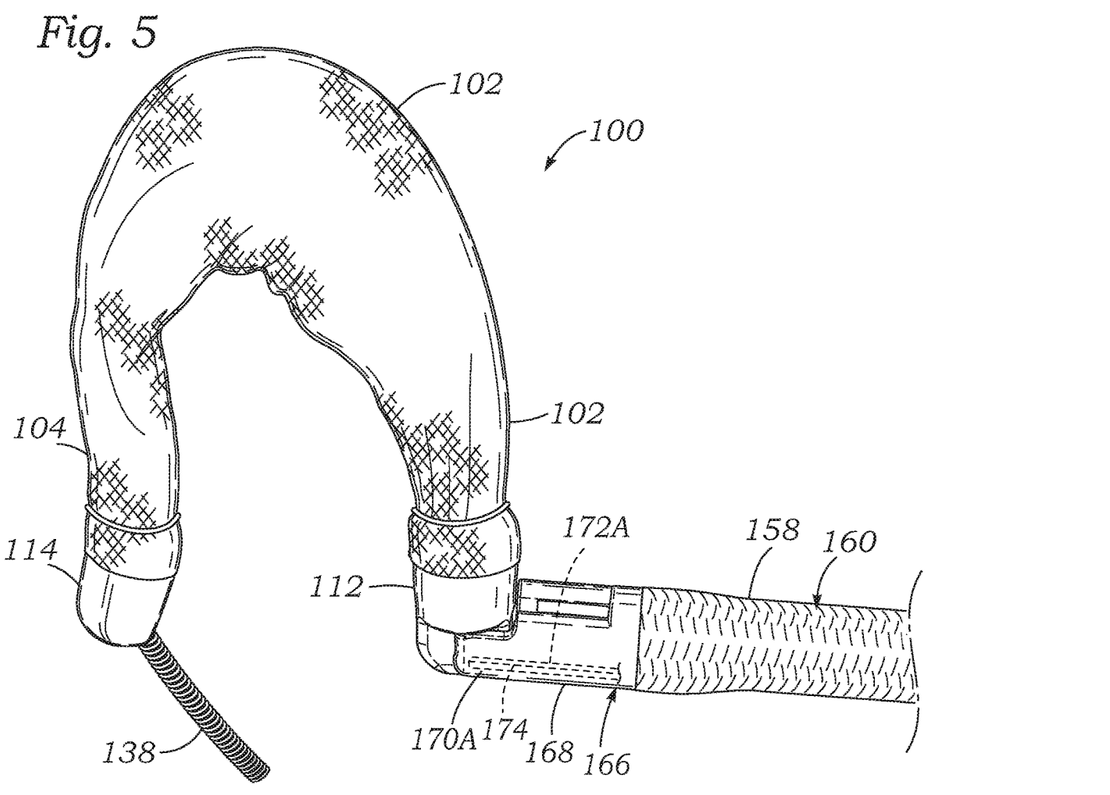
FIG. 5 is a perspective view of the prosthetic device of FIG. 1 coupled to a delivery catheter.

With reference to FIG. 5, in the delivery configuration, the implant 100 can be coupled to a shaft 158 of a first catheter configured as a delivery catheter 160. In some embodiments, the delivery catheter 160 can be disposed coaxially within a delivery sheath (not shown) configured to constrain the implant 100 in a relatively straight and radially collapsed configuration for insertion through a patient's vasculature to the treatment site. When the implant 100 reaches the treatment site, it can be advanced from the delivery sheath, and can assume its functional configuration, as shown in FIG. 5.

Figure 6:
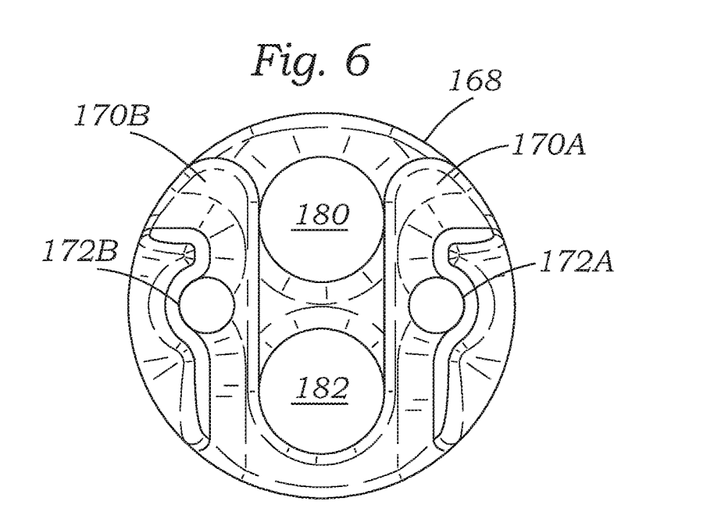
FIG. 6 is an elevation view of a distal end portion of the delivery catheter of FIG. 5.
Figure 7:
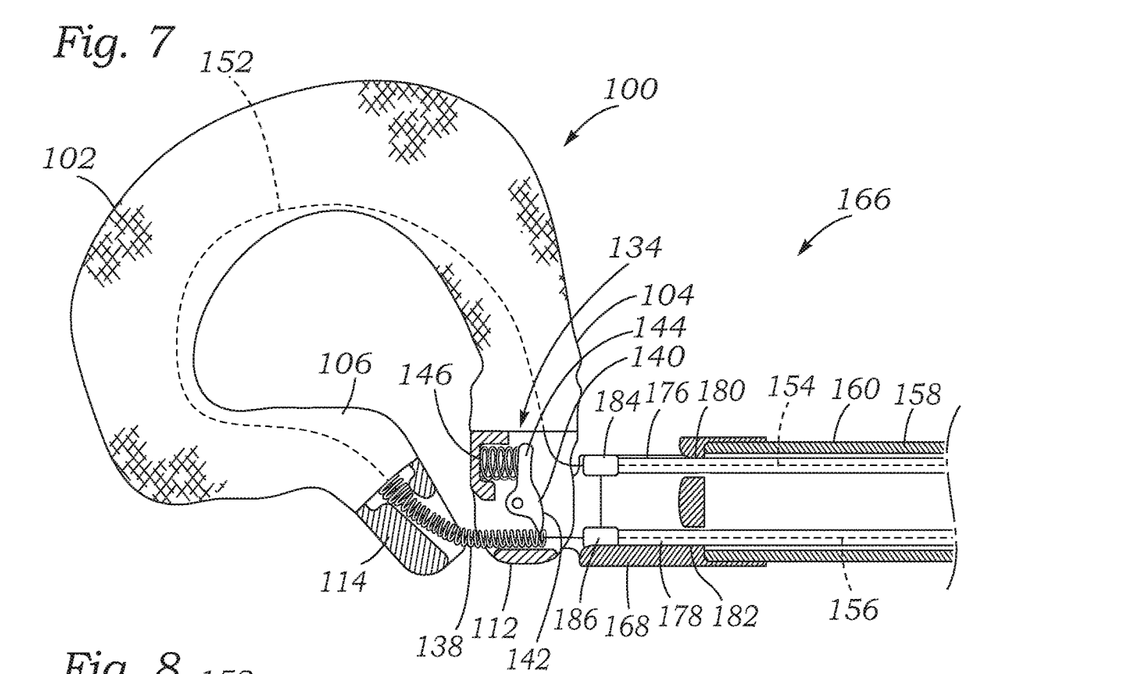
FIG. 7 is a side view of the prosthetic device of FIG. 1 and the delivery catheter of FIG. 5 with the cap members of the prosthetic device and the distal end portion of the catheter shown in cross-section, and with first and second actuator members of the delivery catheter in a proximal position.
Figure 8:
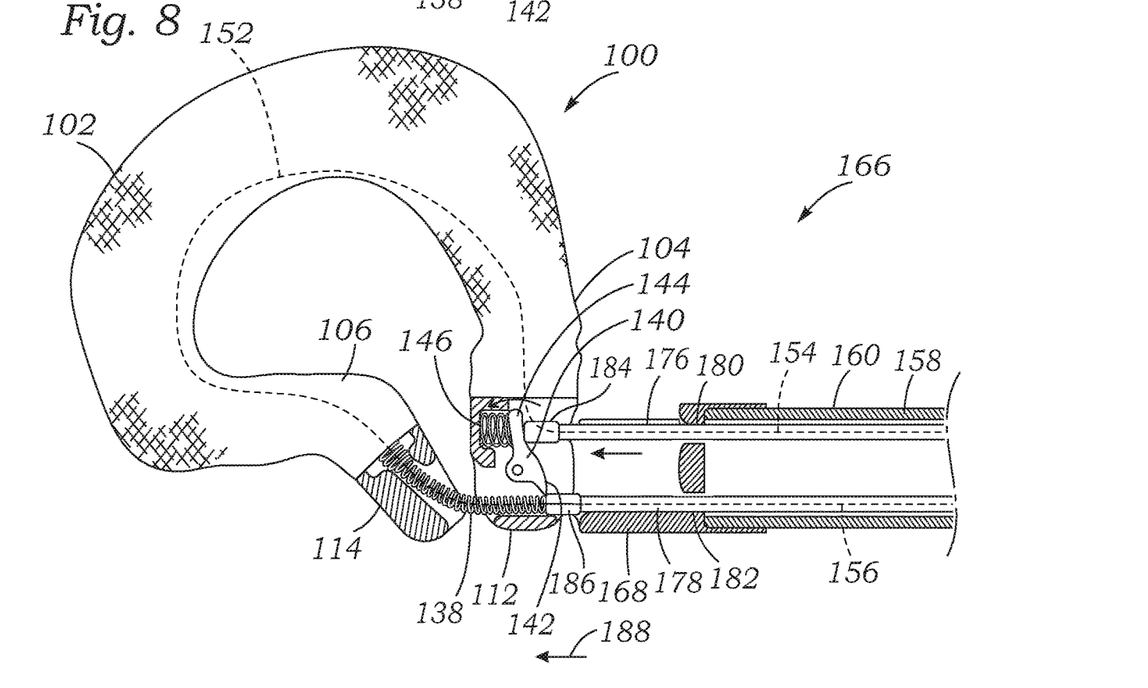
FIG. 8 is a side view of the prosthetic device of FIG. 1 and the delivery catheter of FIG. 5 with the cap members of the prosthetic device and the distal end portion of the catheter shown in cross-section, and with first and second actuator members of the delivery catheter in a distal position.

FIGS. 7 and 8 illustrate a distal end portion 166 of the shaft 158 of the delivery catheter 160 in greater detail. The distal end portion 166 of the shaft 158 can comprise an end portion or cap member 168. The cap member 168 can comprise a pair of extension portions or arms 170A, 170B, which can extend at least partially over the cap member 112 when the shaft 158 is coupled to the implant 100 (arm 170B is hidden from view by the cap member 112 in FIG. 7). As best shown in FIG. 6, the arms 170A, 170B can define respective lumens 172A, 172B. In some examples, a suture thread 174 (indicated in dashed lines in FIG. 5) or other filament can extend from the lumen 172A, transversely through the cap member 112 (e.g., through the opening 115), and back to the cap member 168 through the lumen 172B. In this manner, the implant 100 can be coupled (e.g., tethered) to the delivery catheter 160. In certain configurations, the pivot member 148 can be received in the opening 115, and can define a lumen through which the suture 174 can pass. In some configurations, the implant 100 can be pivotable between the arms 170A, 170B about the pivot member 148 and/or about the suture 174.

The delivery catheter 160 can serve to restrain movement of the cap member 112 relative to the cap member 114. Thus, applying tension to one or both portions 154, 156 of the guide wire 152 can reduce the length of the guide wire within the main body 102 of the implant, as illustrated in FIG. 3. This, in turn, can cause the implant to curl such that the cap member 114 is brought adjacent the cap member 112. In this manner, the coupling member 138, which is coaxially disposed over the guide wire 152, can be received in the cap member 112 such that the pawl member 140 engages the turns 150 of the coupling member. Continued proximal motion of the coupling member 138 through the cap member 112 can tighten the implant by continuing to advance the turns 150 of the coupling member past the pawl member 140 in the manner of a ratchet. In some embodiments, the first end portion 142 of the pawl member 140 can be curved such that downward force on the first end portion causes it to clamp or "bite" onto the turn of the coupling member 138 with which the pawl member is engaged. In this manner, inadvertent distal motion, or motion in the release direction, of the coupling member 138 can be avoided.

Returning to FIGS. 7 and 8, the delivery catheter 160 can also comprise a first actuator member 176 and a second actuator member 178. In the illustrated configuration, the first actuator member 176 can extend through an opening 180 in the cap member 168, and can be movable between a proximal position (FIG. 7) and a distal position (FIG. 8). In the illustrated embodiment, the first portion 154 of the guide wire 152 can extend through a lumen of the actuator member 176 and into the implant 100, although other configurations are possible. In certain configurations, a distal end portion 184 of the actuator member 176 can have a bulb shape to aid in contacting the pawl member 140, as further described below.

In the illustrated configuration, the second actuator member 178 can be located beneath the first actuator member 176, and can also be movable between a proximal position (FIG. 7) and a distal position (FIG. 8) through an opening 182 in the cap member 168. The second portion 156 of the guide wire 152 can extend from the coupling member 138 and into a lumen of the actuator member 178. In some embodiments, a distal end portion 186 of the actuator member 178 can have a bulb shape similar to the actuator member 176, or any other suitable shape, as desired.

Figure 9:
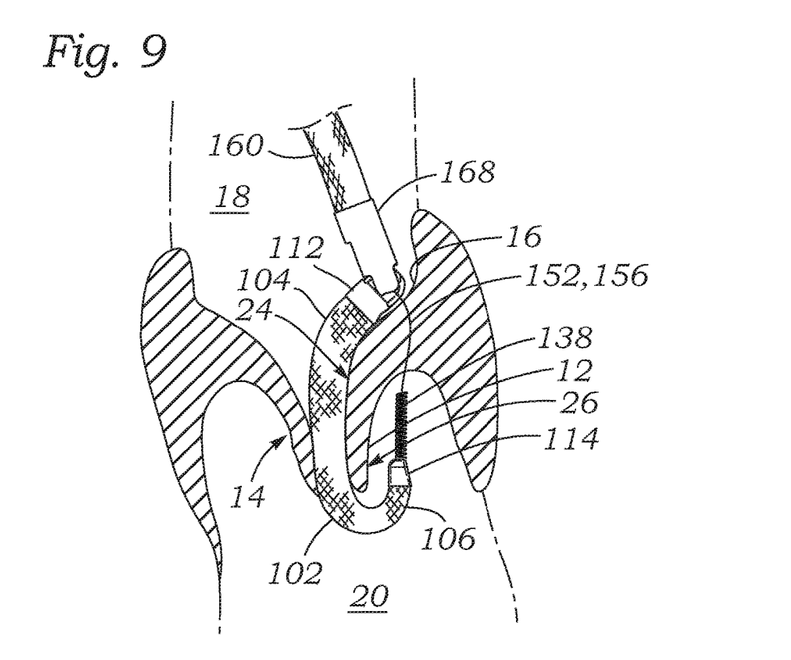
FIG. 9 is a partial cross-sectional view of the mitral valve illustrating the prosthetic device of FIG. 1 situated about the posterior leaflet prior to coupling the first and second end portions of the device together.
Figure 10:
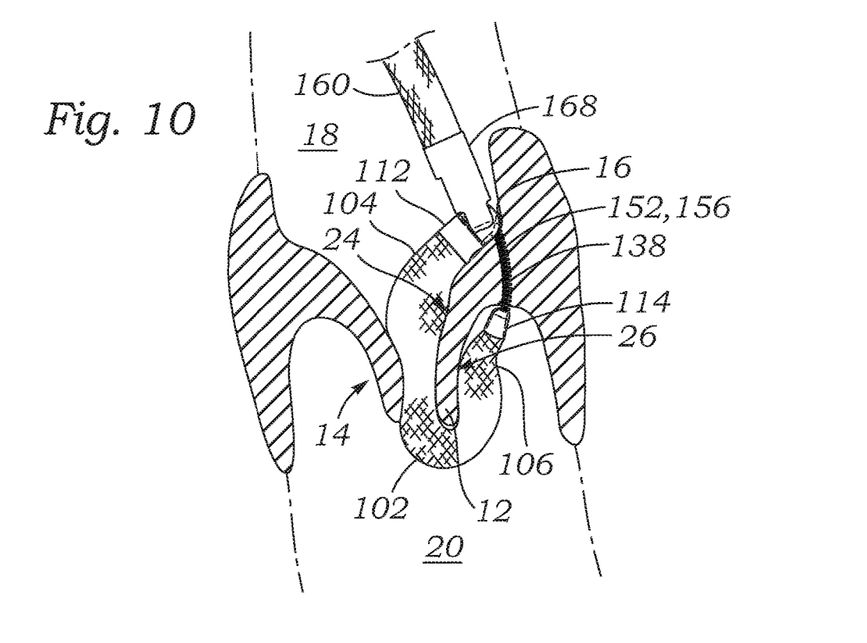
FIG. 10 is a partial cross-sectional view of the mitral valve illustrating the prosthetic device of FIG. 1 situated about the posterior leaflet with the first and second end portions of the device coupled together by the coupling member.

FIG. 9 illustrates the implant 100 disposed around the leaflet 12 prior to coupling the first and second cap members 112, 114 together. In FIG. 9, the cap member 112 is disposed on the atrial surface 24 of the leaflet 12 adjacent the annulus 16, and is coupled to the cap member 168 of the delivery catheter 160. The main body 102 extends over the leaflet 12, and the cap member 114 is located in the left ventricle 20 on the ventricular side of the leaflet adjacent the ventricular surface 26 of the leaflet. By tensioning one or both of the portions 154, 156 of the guide wire 152, the cap member 114 can be drawn adjacent the ventricular surface 26 of the leaflet 12 while the cap member 112 is held stationary by the delivery catheter 160. The coupling member 138 can track over the guide wire 152 such that it extends through the tissue of the leaflet, and emerges on the atrial side of the leaflet adjacent the cap member 112. Further tensioning of the guide wire 152 can draw the coupling member 138 into the cap member 112 such that the coupling assembly 136 engages the coupling member, as illustrated in FIG. 10.

Referring again to FIG. 8, the first actuator member 176 can be configured such that when it is advanced to the distal position, the distal end portion 184 of the actuator member can contact the second end portion 144 of the pawl member 140. This can compress the spring member 146, causing the pawl member 140 to pivot to the second position and disengage from the coupling member 138. When the pawl member 140 is disengaged from the coupling member 138, the second actuator member 178 can be advanced distally. The distal end portion 186 of the second actuator member 178 can be configured to contact the end portion 116 of the coupling member 138. Further distal motion of the actuator member 178 can move the coupling member 138 past the pawl member 140 in the direction of arrow 188 (e.g., back in the direction of the left ventricle 20).

In this manner, the position of the coupling member and, thereby, the degree of curvature of the implant 100 and/or the relative positions of the first and second end portions 104 and 106, can be adjusted. Tensioning of the guide wire 152 can draw the coupling member 138 proximally past the pawl member 140, clamping the leaflet between the cap members 112, 114 and causing the main body 102 to conform to the shape of the leaflet 12. Coaptation of the leaflets and the implant, and/or regurgitation through the valve, can then be assessed. If it is desired to adjust the position of the implant, the pawl member 140 can be disengaged from the coupling member 138 using the actuator member 176, and the coupling member can be pushed back in the direction of the left ventricle 20 through the cap member 112 using the actuator member 178. This process can be repeated until the desired positioning of the prosthetic device 100 is achieved. The coupling member 138 can also be pushed out of the cap member 112 entirely in situations where, for example, it is desired to remove the implant 100.

When the clinician is satisfied with the placement of the implant 100, the delivery catheter 160 can be disengaged from the cap member 112 by withdrawing the suture 174. The guide wire 152 can also be withdrawn from the main body 102, leaving the implant in place on the leaflet 12, as illustrated in FIG. 1.

In other embodiments, the coupling member 138 need not be a coil, but can be configured, for example, as a solid, flexible (e.g., polymeric) member comprising a plurality of ridges, recesses, score lines, teeth, etc., along its length that can engage the pawl member 140, and defining a lumen to receive the guide wire 152. The coupling assembly 136 can also be configured in a variety of different ways. For example, in other embodiments, the pawl member 140 can be a tab member integrally formed with the cap member 112 and configured to engage the coupling member as described above.

General Considerations

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the terms "coupled" and "associated" generally mean electrically, electromagnetically, and/or physically (e.g., mechanically or chemically) coupled or linked and does not exclude the presence of intermediate elements between the coupled or associated items absent specific contrary language.

It should be understood that the disclosed embodiments can be adapted for use with any of the native valves of the heart (e.g., the pulmonary, mitral, and tricuspid valves), and can be used with any of various approaches (e.g., retrograde, antegrade, transseptal, transventricular, transatrial, etc.).

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device toward the user, while distal motion of the device is motion of the device away from the user. The terms "longitudinal" and "axial" refer to an axis extending in the proximal and distal directions, unless otherwise expressly defined.

As used herein, the terms "integrally formed" and "unitary construction" refer to a construction that does not include any welds, fasteners, or other means for securing separately formed pieces of material to each other.

In view of the many possible embodiments to which the principles of the disclosed technology may be applied, it should be recognized that the illustrated embodiments are only preferred examples and should not be taken as limiting the scope of the disclosure. Rather, the scope of the disclosure is at least as broad as the following claims.

The invention claimed is:

1. An implantable heart valve device, comprising:
a main body including a first end portion and a second end portion, the main body being configured to be implanted around a native leaflet of a heart valve such that the first end portion is on an atrial side of the leaflet and the second end portion is on a ventricular side of the leaflet such that the main body can coapt with and move away from an opposing native leaflet during operation of the heart valve;
wherein one of the first or second end portions comprises a coupling assembly;
wherein the other of the first or second end portions comprises a coupling member configured to extend through the native leaflet when the heart valve device is implanted in a heart valve, and the coupling assembly is configured to releasably engage the coupling member to permit adjustment of the relative positions of the first and second end portions;
wherein the coupling assembly comprises a pawl member pivotable between a first position and a second position, the pawl member being configured to engage the coupling member when the pawl member is in the first position; and
wherein the coupling assembly further comprises a spring member configured to bias the pawl member toward the first position.

2. An assembly, comprising:
an implantable heart valve device including a main body having a first end portion and a second end portion, the main body being configured to be implanted around a native leaflet of a heart valve such that the first end portion is on an atrial side of the leaflet and the second end portion is on a ventricular side of the leaflet such that the main body can coapt with and move away from an opposing native leaflet during operation of the heart valve, the first end portion comprising a coupling assembly, and the second end portion comprising a coupling member configured to extend through the native leaflet when the heart valve device is implanted in a heart valve, the coupling assembly being configured to releasably engage the coupling member to permit adjustment of the relative positions of the first and second end portions; and a catheter including a shaft having a distal end portion releasably couplable to the first end portion of the heart valve device;

wherein the catheter comprises a first actuator member movable between a proximal position and a distal position to selectively engage the coupling assembly such that the coupling assembly disengages from the coupling member when the first actuator member is in the distal position;

wherein the coupling assembly comprises a pawl member movable between a first position and a second position, the pawl member being configured to engage the coupling member when the pawl member is in the first position; and wherein the first actuator member is configured to move the pawl member to the second position when the first actuator member engages the pawl member.

3. The assembly of claim 2, wherein the catheter further comprises a second actuator member movable between a proximal position and a distal position to selectively engage the coupling member.

4. The assembly of claim 3, configured such that distal motion of the second actuator member causes corresponding distal motion of the coupling member relative to the coupling assembly when the second actuator contacts the coupling member and the pawl member is in the second position.

5. A method, comprising:
delivering an implantable heart valve device to a native heart valve of a patient's body via a guide wire formed in a loop and extending through a leaflet of the native heart valve such that first and second ends of the guide wire are located outside the patient's body;

positioning a first end portion of the heart valve device on an atrial side of the leaflet, the first end portion including a coupling assembly;

positioning a second end portion of the heart valve device on a ventricular side of the leaflet such that a main body of the heart valve device can coapt with and move away from an opposing native leaflet during operation of the heart valve, the second end portion including a coupling member; and coupling the first end portion of the heart valve device to the second end portion of the heart valve device by inserting the coupling member through the leaflet such that the coupling assembly engages the coupling member.

6. The method of claim 5, wherein:
the coupling assembly comprises a pawl member;
the coupling member comprises a coil member;
and coupling the first and second end portions of the prosthetic device further comprises moving the coil member past the pawl member.

7. The method of claim 6, further comprising uncoupling the pawl member from the coil member with a first actuator member of a delivery catheter coupled to the heart valve device.

8. The method of claim 7, further comprising moving the coupling member in a direction toward the second end portion using a second actuator member of the delivery catheter.

9. An implantable heart valve device, comprising:
a main body including a first end portion and a second end portion, the main body being configured to be implanted around a native leaflet of a heart valve such that the first end portion is on an atrial side of the leaflet and the second end portion is on a ventricular side of the leaflet such that the main body can coapt with and move away from an opposing native leaflet during operation of the heart valve;

wherein one of the first or second end portions comprises a coupling assembly;

wherein the other of the first or second end portions comprises a coupling member configured to extend through the native leaflet when the heart valve device is implanted in a heart valve, and the coupling assembly is configured to releasably engage the coupling member to permit adjustment of the relative positions of the first and second end portions;

wherein the coupling assembly comprises a pawl member pivotable between a first position and a second position, the pawl member being configured to engage the coupling member when the pawl member is in the first position; and wherein the coupling member comprises a coil having a plurality of turns.

10. The implantable heart valve device of claim 9, wherein:
the pawl member and the spring member are situated in a first cap member coupled to the first end portion of the implantable heart valve device; and the coupling member is coupled to a second cap member coupled to the second end portion of the implantable heart valve device.

11. The implantable heart valve device of claim 10, wherein the pawl member is pivotable about a pivot member disposed in the first cap member.

12. The implantable heart valve device of claim 10, wherein the first cap member is in fluid communication with the main body such that a guide wire can extend from the first cap member into the main body.

13. The implantable heart valve device of claim 12, wherein the coupling member defines a lumen such that the guide wire can extend through the lumen of the coupling member.

14. An assembly, comprising:
an implantable heart valve device including a main body having a first end portion and a second end portion, the main body being configured to be implanted around a native leaflet of a heart valve such that the first end portion is on an atrial side of the leaflet and the second end portion is on a ventricular side of the leaflet such that the main body can coapt with and move away from an opposing native leaflet during operation of the heart valve, the first end portion comprising a coupling assembly, and the second end portion comprising a coupling member configured to extend through the native leaflet when the heart valve device is implanted in a heart valve, the coupling assembly being configured to releasably engage the coupling member to permit adjustment of the relative positions of the first and second end portions; and a catheter including a shaft having a distal end portion releasably couplable to the first end portion of the heart valve device;

wherein the distal end portion of the catheter member is releasably coupled to the first end portion of the heart valve device by suture;

wherein the first end portion of the heart valve device comprises a cap member;

wherein the distal end portion of the catheter comprises first and second arm portions; and wherein the suture extends from a lumen defined in the first arm portion, through the cap member, and through a lumen defined in the second arm portion.

15. An assembly, comprising:

an implantable heart valve device including a main body having a first end portion and a second end portion, the main body being configured to be implanted around a native leaflet of a heart valve such that the first end portion is on an atrial side of the leaflet and the second end portion is on a ventricular side of the leaflet such that the main body can coapt with and move away from an opposing native leaflet during operation of the heart valve, the first end portion comprising a coupling assembly, and the second end portion comprising a coupling member configured to extend through the native leaflet when the heart valve device is implanted in a heart valve, the coupling assembly being configured to releasably engage the coupling member to permit adjustment of the relative positions of the first and second end portions; and a catheter including a shaft having a distal end portion releasably couplable to the first end portion of the heart valve device; and a guide wire extending from the catheter, through the main body of the heart valve device, through the coupling member, and back into the catheter.

* * * * *